(12) United States Patent
Westerlund

(10) Patent No.: US 7,140,770 B2
(45) Date of Patent: Nov. 28, 2006

(54) ARRANGEMENT RELATED TO A DENTAL SENSOR

(75) Inventor: Jan Westerlund, Trollhattan (SE)

(73) Assignee: Jan E. Westerlund AB, Trollhattan (SE)

( * ) Notice: Subject to any disclaimer, the term of this patent is extended or adjusted under 35 U.S.C. 154(b) by 0 days.

(21) Appl. No.: 10/522,838

(22) PCT Filed: Aug. 4, 2003

(86) PCT No.: PCT/SE03/01249

§ 371 (c)(1),
(2), (4) Date: Feb. 2, 2005

(87) PCT Pub. No.: WO2004/013691

PCT Pub. Date: Feb. 12, 2004

(65) Prior Publication Data

US 2005/0259792 A1   Nov. 24, 2005

(30) Foreign Application Priority Data

Aug. 5, 2002   (SE) .................................... 0202371

(51) Int. Cl.
*A61B 6/14* (2006.01)
(52) U.S. Cl. ....................... 378/170; 378/168; 378/169; 378/191

(58) Field of Classification Search ........ 378/168–170, 378/191
See application file for complete search history.

(56) References Cited

U.S. PATENT DOCUMENTS

| 4,365,162 | A |   | 12/1982 | Jarby |
| 4,507,798 | A |   | 3/1985 | Welander |
| 4,554,676 | A | * | 11/1985 | Maldonado et al. ........ 378/170 |
| 4,598,416 | A | * | 7/1986 | Donato ........................ 378/168 |
| 4,941,164 | A | * | 7/1990 | Schuller et al. ............. 378/205 |
| 5,090,047 | A | * | 2/1992 | Angotti et al. ............... 378/170 |
| 5,202,911 | A | * | 4/1993 | Fabian ........................ 378/168 |
| 5,289,522 | A |   | 2/1994 | Kanbar et al. |

* cited by examiner

*Primary Examiner*—Edward J. Glick
*Assistant Examiner*—Jurie Yun
(74) *Attorney, Agent, or Firm*—Mark P. Stone

(57) ABSTRACT

The present invention pertains to an arrangement relating to a sensor plate for dental X-raying or photographic purposes, wherein the plate (10;10';10";10''') for example is of a digital or analogue type and is intended for one-time use or for many-times use. The sensor plate (10;10';10";10''') includes or carries elements (30,31;30',31";61–64;80–82; 90;95) that are intended for engagement with a plate holding element (40) in a number of different positions (A–F). The holding element (40) includes means (51,52;50) for engagement with engagement elements (30,31;30,31';61–64;80–82;90;95) of the sensor plate.

20 Claims, 4 Drawing Sheets

ARRANGEMENT RELATED TO A DENTAL SENSOR

The present invention relates to an arrangement concerning a sensor plate for taking dental X-rays in accordance with the preamble of Claim 1. The invention also relates to a holder for positioning the sensor plate in dental X-ray operations.

Several different types of auxiliary devices are known in the art for holding or supporting a sensor plate or an X-ray plate/X-ray film in connection with dental X-ray operations. Such devices are based on the use of a square, flat sensor plate or X-ray film, wherein the auxiliary device includes different types of means for engagement with the plate/film such as to hold the sensor in the position desired when taking a dental X-ray. Alternative options are desired with regard to holding/supporting the plate/film depending on where the plate shall be placed in the oral cavity, i.e. depending on which tooth or which teeth that shall be examined and X-rayed.

The use of multi-use sensor plates has become more usual in the profession. The sensor plates are normally digital, although analogue plates are also conceivable. The term sensor plate as used in the present context shall therefore be understood as meaning an auxiliary device for presenting a translucent image or X-ray image that is normally presented electronically and saved in an appropriate manner.

An object of the present invention is to provide an extraordinarily attractive sensor plate arrangement of the above mentioned type, said object being achieved with the sensor plate and the arrangement defined in the characterising clauses of the claims.

The inventive sensor plate arrangement provides both technical and economical advantages.

According to the present invention, the sensor plate includes mutually separate elements for co-action with the holder in a number of mutually different ways, such as provide a large number of positioning options in the performance of dental examinations.

The present invention will now be described in more detail with reference to exemplifying embodiments thereof and also with reference to the accompanying drawings, in which FIG. 1 is a composite perspective view of an inventive arrangement, FIGS. 2–6 are respective perspective views of different embodiments of inventive sensor plates, and FIGS. 7 and 8 are respective side views of a further anchoring alternatives between holder elements and sensor plates.

Shown in FIG. 1 is a dental X-ray sensor plate 10 which may, of course, have any one of a number of designs that lie within the scope of applicable analogue and digital imaging techniques. Those cables that may be required for image transmission purposes have not been shown.

The sensor plate 10 of the FIG. 1 embodiment includes four side strips 21–24, each of which comprises two longitudinally extending guide strips 30 and a transverse guide strip 31. Openings 32 and 33 are disposed between the guide strips 30 and 31. The side strips 21–24 also include an opening or groove 35 which enables the side strips to be fitted to the side edges 11–14 of the sensor plate 10 prior to using said sensor plate. If desired, the side strips 21–24 can be integrated with the sensor plate 10 so as to form a one-piece structure.

Also shown in FIG. 1 is a holder element in the form of a pin 40 which is adapted to co-act with the side strip arrangement of sensor plate 10. The holder pin 40 includes a stem 41, a so-called biting pad or biting plate 45, and strip 50. The stem 41 is connected to the biting pad 45 via a junction 42. The strip 50 includes a longitudinally extending groove 51 and a transverse groove 52. The holder/holder pin 40 also includes an aligning pin 46 which is intended to function as an alignment assist in taking photographs or carrying out X-ray examinations.

In the performance of a dental X-ray, the sensor plate 10 carrying the side strips 21–24 can be fitted to the holder/holder pin 40 in two different ways. This is made possible by engagement of the longitudinal groove 51 with two mutually opposing guide strips 31 on the side strips 21 and 23 or on the side strips 22 and 24. The sensor plate 10 carrying the side strips 21–24 can also be fitted to the holder pin 40 in an additional four ways, by virtue of the engagement of the longitudinal groove 51 with the longitudinal guide strips 30 on one of the side trips 21–24, wherewith the transverse groove 52 receives the transverse strip 31. These assembly options mean that the holder pin 40 can be fitted to the sensor plate 10 in any one of six different ways, thereby enabling the sensor plate to be orientated as desired in the patient's mouth in connection with a dental X-ray. The patient can assist in the fixation of the sensor plate 10 in its desired position, by biting on the biting plate or pad 45. The alignment pin 46 functions to assist in the alignment of the radiation source used in the X-ray process or the photographic process concerned.

Figure 1:
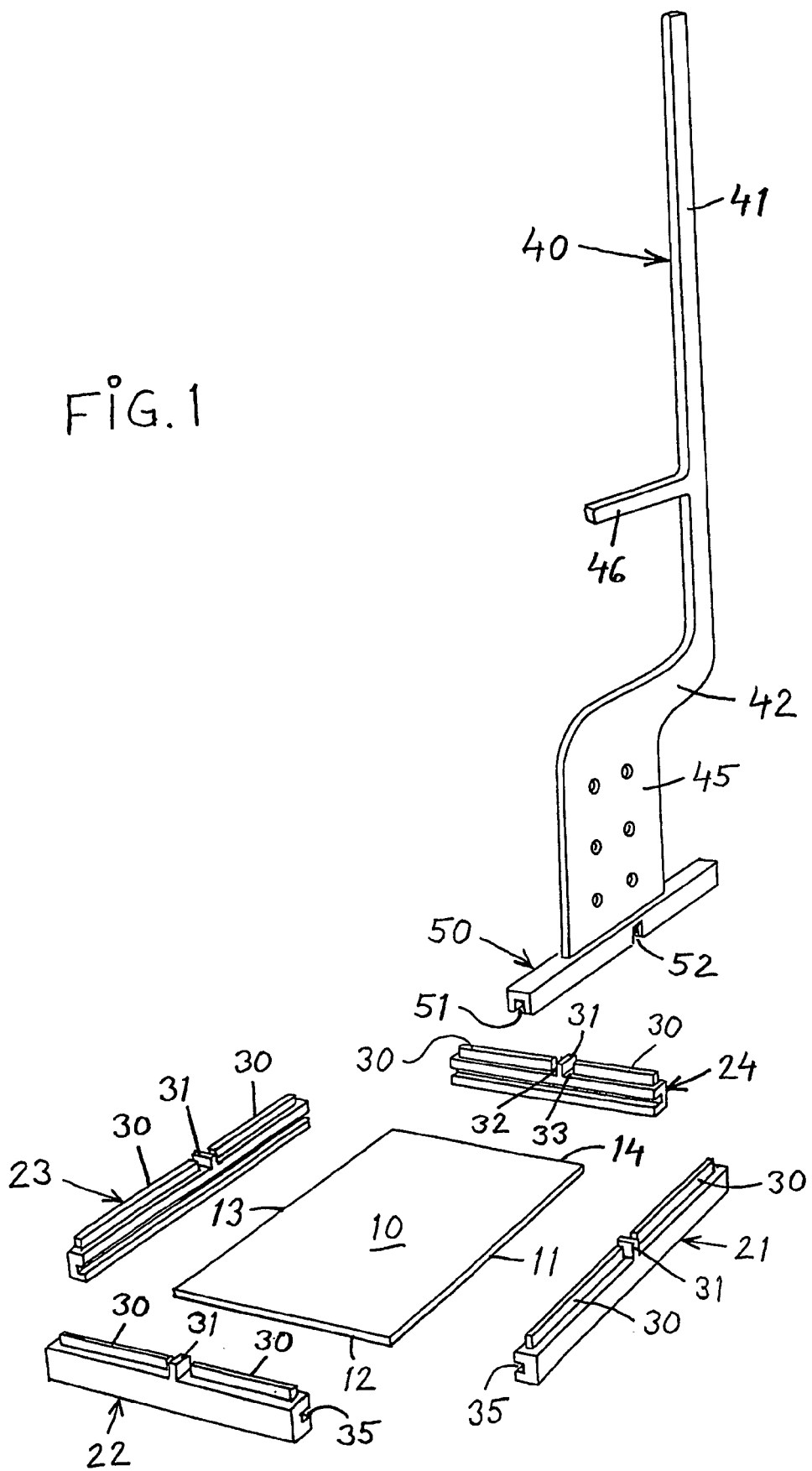
Figure 2:
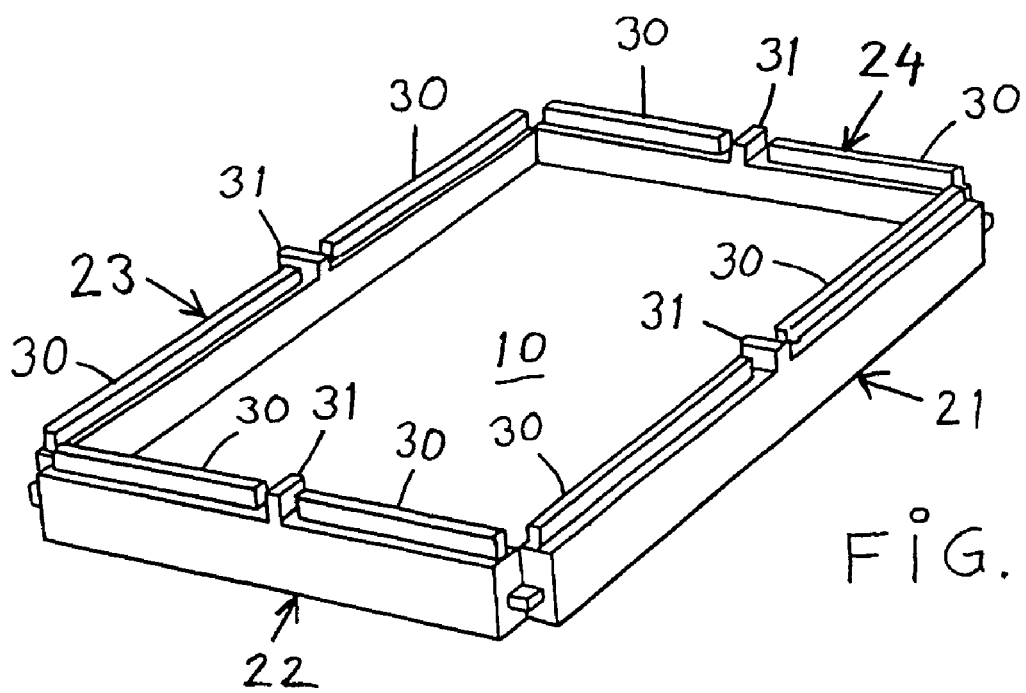
FIG. 2 shows the sensor plate 10 with the side strips 21–24 attached thereto.
Figure 3:
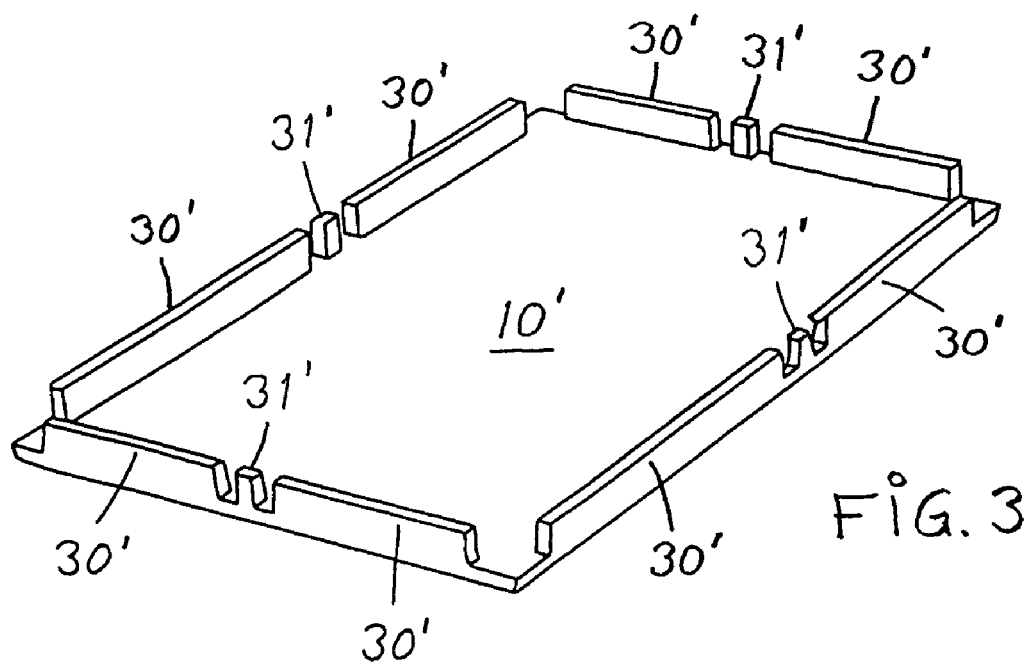
FIGS. 3–5 illustrate examples of alternative embodiments of inventive sensor plates.

In the case of the sensor plate 10' shown in FIG. 3, the longitudinal strips 30' and the transverse strips 31' are integral with the sensor plate 10' and therewith fixed parts thereof.

Figure 4:
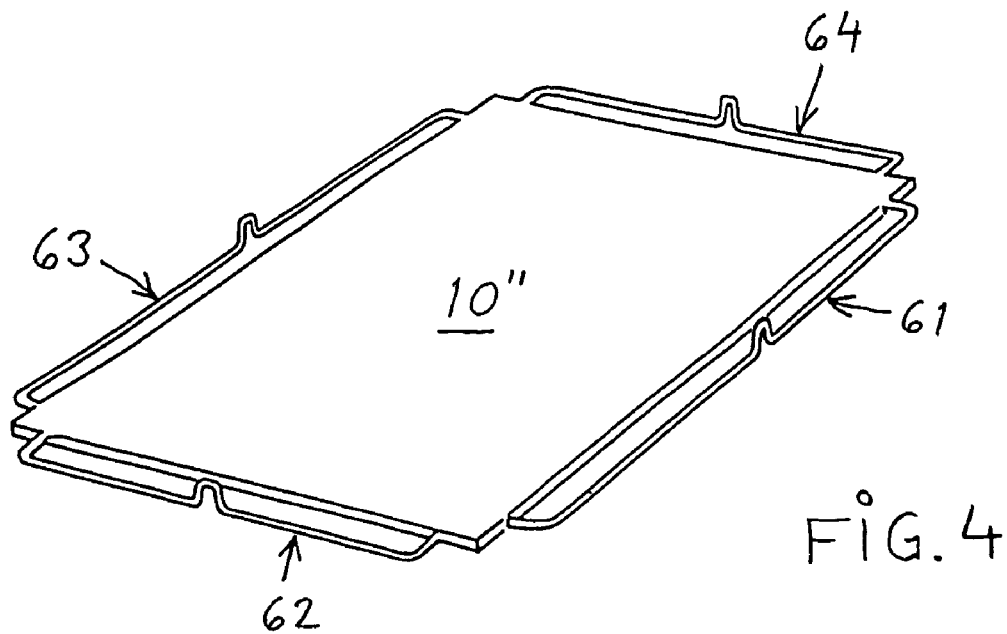

In the case of the sensor plate 10" shown in FIG. 4, the plate carries wire-like side elements 61–64 that are adapted for co-action with the grooves 51 and 52 in the holder 40.

Figure 5:
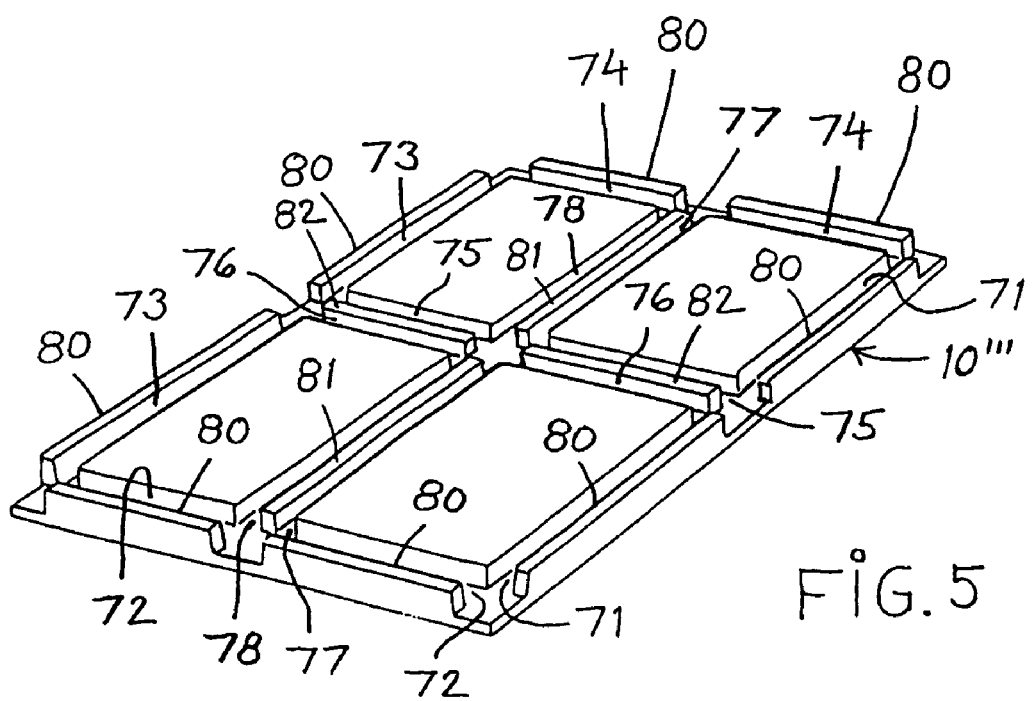

In the case of the sensor plate 10'" shown in FIG. 5, the plate includes openings 71–78 or grooves that provide the necessary holder engagement or connection means 80–82, said means 80–82 engaging the longitudinal groove 51 in the holder 40.

It will be noted that the embodiments shown in FIGS. 3–5 also provide six different options in fitting the sensor plate to the holder 40.

Figure 6:
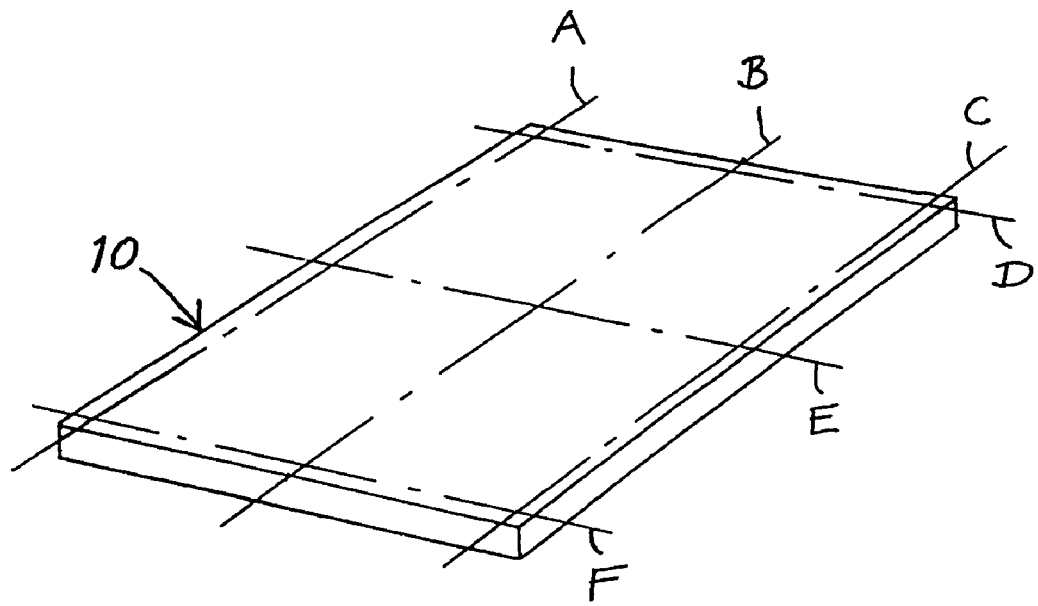

The optional possibilities of fitting the holder to the sensor plate 10 in accordance with the invention are shown in chain lines A–F in FIG. 6.

Figure 7:
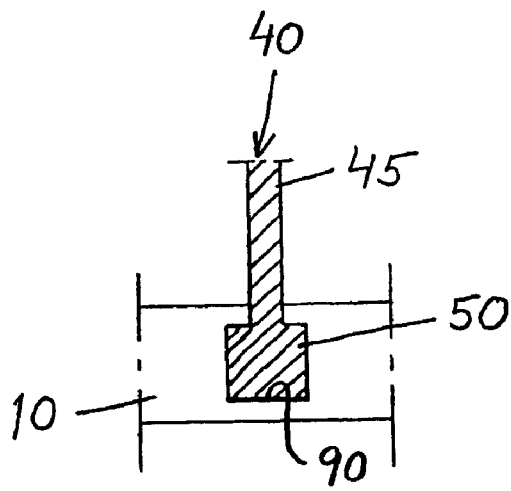

FIG. 7 illustrates alternative means of securing the holder 40 to the sensor plate 10. In this case, the holding strip 50 fits essentially shape-wise into a groove 90 in the sensor plate, wherein the plate 10 will preferably include a groove pattern according to the lines A–F in FIG. 6. The plate holding strip 50 is thus inserted into an appropriate groove 90, in the performance of a dental examination.

Figure 8:
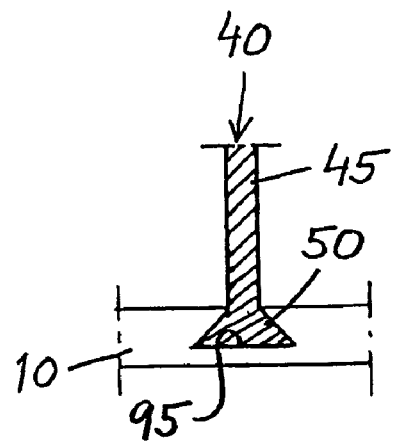

FIG. 8 illustrates a further alternative securing of the holder 40 to the sensor plate 10, where the holding strip 50 fits essentially shape-wise into a groove 95 in the sensor plate, wherein the sensor plate 10 preferably include a groove pattern according to the lines A--F in FIG. 6. The plate holding strip 50 is thus inserted into an appropriate groove 95, in the performance of a dental examination.

It will be understood that many options are available with regard to the design of the inventive sensor plate for co-action with the holder. It will thus be understood that both the sensor plate and the plate holder can be modified in many different ways within the concept of the invention. An essential feature, however, is that the sensor plate carries means for connecting the plate to a holder pin or to a holding element, said means being either fixed or detachable.

It will further be noted that the holding pin and the side strips may be made of any appropriate material, such as a plastic material as a non-limiting example. Moreover, the sensor plate and its inventive side surface or edge arrangement and/or its arrangement of openings may be covered with a replaceable protective casing of a one-time nature or of a nature that enables the sensor plate to be used a few times while maintaining the necessary level of hygiene with regard to dental examinations. The holding pin may be of a one-time nature or may be reusable many times, depending on the material from which it is made and also on available possibilities for sterilisation or disinfection.

When the sensor plate engagement elements are removable, these elements can also be made from a material that can be sterilised or disinfected effectively. If so wished, the sensor plate, inclusive of the engagement means, can be designed to enable the same to be sterilised and disinfected effectively.

If the holder 40 is intended for one-time use only, the holder will preferably be dimensioned to hold the plate in respect of all exposures required with regard to one and the same patient in the process of a dental examination.

It will be noted that in the case of a simplified embodiment of the invention, the sensor plate may be adapted to engage the holder in three different positions, for instance in the positions A,C,E or B,D,F or in other positional combinations. This is achieved by reducing the number of engagement elements on the sensor plate. Thus an essential feature of the invention is that the sensor plate includes, carries or is equipped with elements that can engage a plate holding element in at least three different positions, preferably in six different positions. If so wished, the sensor plate may, of course, be designed to engage a plate holding element in four or five different positions, by the above mentioned reduction in the number of engagement elements on the sensor plate.

It will of course be understood that design modifications are possible within the framework of the inventive concept. The outer configuration of the sensor plate and the design of the plate holding element may, of course, be varied.

Many variations are possible within the scope of the invention, with regard to the detail arrangement of the openings in the sensor plate and/or supplementary arrangements, wherewith the design of the plate holding element can also be adapted for desired or necessary positioning co-action.

It will therefore be understood that the present invention is not limited to the described and illustrated embodiments thereof and that changes and modifications are possible within the scope of the accompanying claims.

The invention claimed is:

1. An arrangement for a sensor plate for dental X-raying purposes, wherein said arrangement comprises a sensor plate (10, 10', 10", 10'''), engagement elements (30, 31, 30', 31', 61–64; 80–82; 90; 95), and a plate holding element (40), characterized in that the sensor plate is of a digital or analogue type and is usable one or more times, said sensor plate includes or carries the engagement elements for engagement with said plate holding element in at least three different positions (A–F), and in that said engagement elements are fixed on or arranged in said sensor plate such that the sensor plate is not movable relative to said engagement elements in each of said at least three different positions.

2. An arrangement according to claim 1, characterised in that the engagement elements (30, 31) of the sensor plate are arranged at side elements (21–24).

3. An arrangement according to claim 2, characterised in that the engagement elements (30, 31) are detachable from the sensor plate (10).

4. An arrangement according to claim 2, characterised in that the holding element (40) includes grooves (51, 52) for engagement with the sensor plate engagement elements (30, 31, 30', 31'; 61–64; 80–82).

5. An arrangement according to claim 2, characterised in that the plate holding element (40) includes a biting plate (45).

6. An arrangement according to claim 2, characterised in that the plate holding element (40) includes a holding pin (41) and an alignment assisting element (46).

7. An arrangement according to claim 2, characterised in that the sensor plate (10, 10', 10", 10''') is adapted to engage the holding element (40) in six different positions (A–F).

8. An arrangement according to claim 1, characterised in that the engagement elements (30, 31) are detachable from the sensor plate (10).

9. An arrangement according to claim 8, characterised in that the holding element (40) includes grooves (51, 52) for engagement with the sensor plate engagement elements (30, 31, 30', 31'; 61–64; 80–82).

10. An arrangement according to claim 8, characterised in that the plate holding element (40) includes a biting plate (45).

11. An arrangement according to claim 8, characterised in that the plate holding element (40) includes a holding pin (41) and an alignment assisting element (46).

12. An arrangement according to claim 1, characterised in that the engagement elements comprise wire-like elements (61–64).

13. An arrangement according to claim 1, characterised in that the holding element (40) includes grooves (51, 52) for engagement with the sensor plate engagement elements (30, 31, 30', 31'; 61–64; 80–82).

14. An arrangement according to claim 1, characterised in that the plate holding element (40) includes a biting plate (45).

15. An arrangement according to claim 1, characterised in that the plate holding element (40) includes a holding pin (41) and an alignment assisting element (46).

16. An arrangement according to claim 1, characterised in that the sensor plate (10, 10', 10", 10''') is adapted to engage the holding element (40) in six different positions (A–F).

17. An arrangement for a sensor plate for dental X-raying purposes, wherein said arrangement comprises a sensor plate (10,10', 10", 10'''), engagement elements (30, 31, 30', 31', 61–64; 80–82; 90; 95), and a plate holding element (40), characterized in that the sensor plate is of a digital or analogue type and is usable one or more times, said sensor plate includes or carries the engagement elements for engagement with said plate holding element in at least three different positions (A–F), and in that said engagement elements are fixed on or arranged in said sensor plate, wherein the engagement elements include openings (71–78; 90; 95) in the sensor plate (10''').

18. An arrangement according to claim 17, characterised in that the holding element (40) includes grooves (51, 52) for engagement with the sensor plate engagement elements (30, 31, 30', 31'; 61–64; 80–82).

19. An arrangement according to claim 17, characterised in that the plate holding element (40) includes a biting plate (45).

20. An arrangement according to claim 17, characterised in that the plate holding element (40) includes a holding pin (41) and an alignment assisting element (46).

* * * * *

UNITED STATES PATENT AND TRADEMARK OFFICE
CERTIFICATE OF CORRECTION

| | |
|---|---|
| PATENT NO. | : 7,140,770 B2 |
| APPLICATION NO. | : 10/522838 |
| DATED | : November 28, 2006 |
| INVENTOR(S) | : Jan Westerlund |

Page 1 of 1

It is certified that error appears in the above-identified patent and that said Letters Patent is hereby corrected as shown below:

Column 4, Line 44 (Claim 17, Line 1) :

Delete "X-raving" and substitute --x-raying--.

Signed and Sealed this

Sixth Day of February, 2007

JON W. DUDAS
*Director of the United States Patent and Trademark Office*